United States Patent
Toney et al.

[11] Patent Number: 6,098,249
[45] Date of Patent: Aug. 8, 2000

[54] APPARATUS FOR FORMING CONTROLLED DENSITY FIBROUS PADS FOR DIAPERS AND THE OTHER ABSORBENT PRODUCTS

[76] Inventors: Jerry L. Toney; Nathan E. E. Toney, both of 4450 Duncan Bridge Rd., Cleveland, Ga. 30528; Gerald Najour, 6456 Rosecommon Dr., Norcross, Ga. 30092; Gregory F. Ward, 11115 Rotherick Dr., Alphaaretta, Ga. 30022

[21] Appl. No.: 08/960,412

[22] Filed: Oct. 29, 1997

[51] Int. Cl.[7] .................................................. D01G 25/00
[52] U.S. Cl. .............................. 19/296; 19/301; 403/294; 425/80.1
[58] Field of Search ............................ 19/296, 301, 302; 264/112, 121; 425/80.1, 81.1; 403/292, 294, 401; 29/895.2, 895.3; 492/32, 38, 47; 198/397.03; 209/284, 288, 296, 297, 406, 405, 397, 399, 684, 686

[56] References Cited

U.S. PATENT DOCUMENTS

| | | | |
|---|---|---|---|
| 4,666,647 | 5/1987 | Enloe et al. | 19/308 |
| 5,226,991 | 7/1993 | Svaighert | 19/308 |
| 5,245,728 | 9/1993 | Rupp et al. | 19/308 |
| 5,665,396 | 9/1997 | Ulman | 425/80.1 |
| 5,866,173 | 2/1999 | Reiter et al. | 425/80.1 |

*Primary Examiner*—John J. Calvert
*Assistant Examiner*—Gary L. Welch

[57] ABSTRACT

The present invention provides an improved apparatus for forming a fibrous pad for absorbent products with improved density control. Fibers entrained in a high speed air flow are deposited onto the foraminous surface of a spaced, three-dimensional pad-forming pocket. The fine foraminous pad forming screen is supported on its periphery by two top plates, a coarse forming screen, two subplates and end rails which incorporate a device to hold the pad forming screen.

A gas flow regulating system consisting of precisely placed cross directional fixed and adjustable airflow control louvers controls the air flow direction and reduces spill over and turbulence during the pad formation and especially during the transition of the forming pocket into and out of the air stream as the rotary former shell rotates through the filling position.

Additional control of density and fiber placement is gained through the use of additional gas control innovations including a tapering the pocket ends such that the airflow is streamlined especially during pocket transition through forming sections.

12 Claims, 7 Drawing Sheets a  b  c

35

APPARATUS FOR FORMING CONTROLLED DENSITY FIBROUS PADS FOR DIAPERS AND THE OTHER ABSORBENT PRODUCTS

FIELD OF THE INVENTION

The present invention relates to an apparatus for forming fibrous pads used for absorbent applications such as disposable diapers and the like and more specifically to an apparatus employing a rotating drum containing a modular pad forming system wherein the density of the pad at any point, and especially at the circumferential extremes and across the pad width, is controlled by the use of any combination of specially spaced fixed and adjustable airflow control louvers and other air turbulence reducers located contiguous with or on the down stream side of the foraminous layer which describes the bottom of the forming pocket.

BACKGROUND AND DESCRIPTION OF THE PRIOR ART

This invention relates to an apparatus for forming fibrous pads, from cellulose or other fibers and including all forms of superabsorbent in any fluid conveyable form, for diapers or similar other absorbent products, and more particularly, to an apparatus employing modular foraminous forming pockets which when connected end-to-end form the periphery of a rotatable drum. The modular foraminous forming pockets are associated with both a novel and unique airflow control louver system and a screen support system which provides uniform density control across the axial and lateral dimensions of the pad. By changing the cross section of the airflow control louvers or rotatable secondary louvers appended to the primary air control louvers it is possible to also modify the density and the weight of fibers per square inch of pocket area such that the amount and density of the fibers may be varied over the width and length of the pad.

Rotary forming drums have been known for a considerable time and are in wide use in the production of disposable infant and adult diaper pads, feminine hygiene pads and similar products. Typical examples of these drum formers are described in U.S. Pat. No. 4,859,388 to Peterson et al and U.S. Pat. No. 5,044,052 to Hertel et al. Typical rotary drum type pad forming systems use a fixed outer drum to which pad forming pockets are attached and radial support struts positioned under the forming wires or screens. These supports are typically spaced about 6 to 10 radial degrees apart, measured at the inside diameter of a typical 46 inch diameter drum. Typically, in the prior art, they are not described as being specifically used for altering or otherwise modifying the air flow through the pad. Problems typically encountered in the aforesaid configuration are uneven fiber density in the pad, especially at the ends, and clumping due to scarfing of the pad by high velocity air tangent to the screen. This problem is primarily due to the wide spacing of the support struts which induces turbulence during the transition of the pad ends from a low pressure plenum to a higher pressure plenum.

It is well known in the patent art that in order to obtain high pad integrity it is necessary to have a high air flow through the pad during forming sequence. However, the large volume of air produces air turbulence and instability especially at the ends and edges of the forming pocket and, consequently, the fiber distribution problems described above occur. These instabilities are usually seen as eddies or pulsing at the extreme pad ends as the pocket ends transition into or from the low pressure source. Further, the sides of the pads are also disturbed by the development of local edge turbulence because the solid or non-foraminous pocket sides are not able to adequately vent the forming air.

Considerable investigation into the aerodynamics of the forming system indicated that, contrary to the current commercial practice of having the number of radial support struts minimized, a large and unexpected improvement in the density and uniformity of the whole pad and especially the pad ends and sides was produced by using airflow control louvers in place of supports and spacing the airflow control louvers at three radial degrees based on a the 46 inch inside diameter of the standard drum former.

It was also determined by experimentation that when the lateral cross section of the louver was modified such that lateral radial surface was made concave or convex in the lateral direction the resulting air flow was altered sufficiently to change the lateral cross sectional profile of the pad. Similar effects were noted when the lateral cross section of the louver was modified such that lateral radial surface was made concave or convex in the radial direction the resulting air flow was altered sufficiently to change the lateral cross sectional profile of the pad.

A further invention, which also contributes to a significant reduction in turbulence at the pocket ends, is the use of an innovative method of end rail design. This consists of tapering the end rails so that they do not disturb the air flow and present a more aerodynamic surface as compared to the typical blunt edge used in pad former supports. This design virtually eliminates turbulence caused by conventional stepedged rails.

A further invention was discovered by off-setting the sub-plate support system at its internal circumferential edges. This created an opening to permit the venting or passage of air along the vertical height of the forming pocket and reduced air turbulence to a minimum.

The current invention is aimed at a simple and cost effective means for forming uniform fluff pads with high pad integrity. This is advantageously applied to a drum-style former especially since the overall design of the modular pocket assembly permits the construction of a totally self-supporting outside drum with no side supports. This provides a unique capability to create a free standing and totally self-supporting drum assembly by use of modular pockets placed end-to-end and permits the easy adaptation of the system to competitive drum former suction internals and drive shaft assemblies. The self support system is accomplished by the use of a novel concentricity stabilizer which permits construction of the individual modular pocket assemblies into a perfectly circular drum ready for attachment to suitable drum flanges or discs and shaft assemblies for installation on virtually any pad forming line.

It should be recognized that the pad former pocket construction concept is not limited to drum formers but can be adapted to other former configurations including linear endless "belt" systems.

In evaluations of competitive equipment before modification with the modular pad former system it was determined that, in addition to the air turbulence problems detailed above, the pressure profile across the width of the drum below the inner diameter of the drum had significant variations due to problems with the internal low pressure side design. This resulted in variations in fiber density and the amount or weight of fiber per square inch across the pad width.

A further invention that eliminated this problem is a unique adjustable airflow control louver. This airflow control louver can modify air flow across the width of the modular pad former system. The adjustable side of the airflow control louver is rotatable around its hinge point thereby reducing or otherwise altering, in a controllable and desirable manner, the pattern of air flow between any two airflow control louvers. The airflow control louver is rotated until the required results are achieved and then locking it in place by a locking means. It was discovered that when the adjustable portion of the airflow control louver was modified such that its radial length diminished at a uniform rate across the width of the pad former in the correct conformity that the density and amount of fiber per square inch could be made uniform. Other adjustable airflow control louver profiles provide further control and modification of density and weight per square inch.

A further invention is the tilt lock screen strap system which provides a positive method for locking the ends of the inner and outer foraminous layers in place without tearing or damaging them. This consists of a hold down strap which fits into a horizontal slot milled into the outer surface of each end plate. The lower surface of the slot is further divided into two depths. The plate is clamped in place by a screw or other fastening device which penetrates the lower milled surface of the slot. The tilt lock strap or plate end farthest from the screen ends rests on the apical section of the slot which acts as a pivot point for the strap when the fastening means is tightened thus providing a leverage to the plate, which translates into a high linear locking pressure on the screens at their outer ends.

DESCRIPTION OF THE INVENTION

The invention is described in conjunction with an illustrative embodiment in the accompanying drawings in which.

DETAILED DESCRIPTION OF THE PREFERRED EMBODIMENTS

Figure 1:
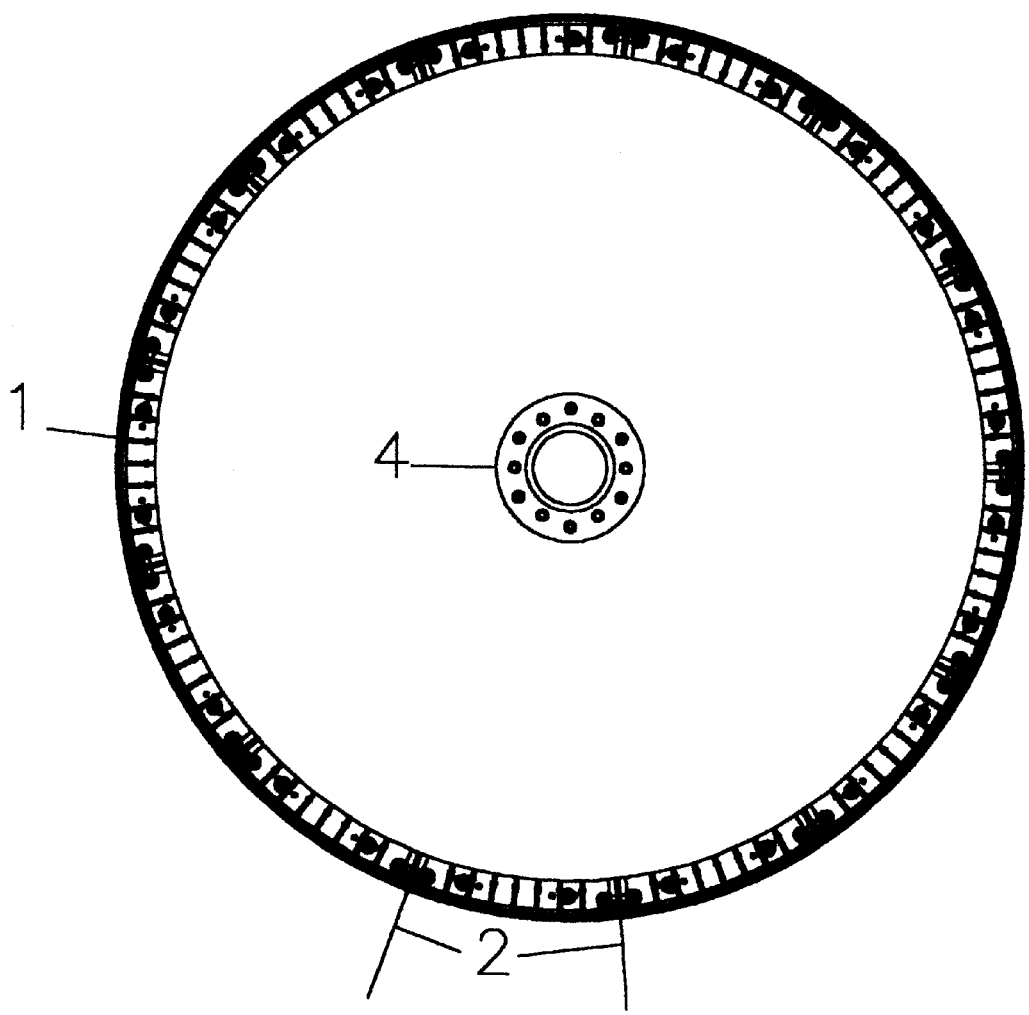
FIG. 1 is a side elevational view of apparatus employed in the practice of the invention and illustrates the assembly of the pad forming modules.
Figure 2:
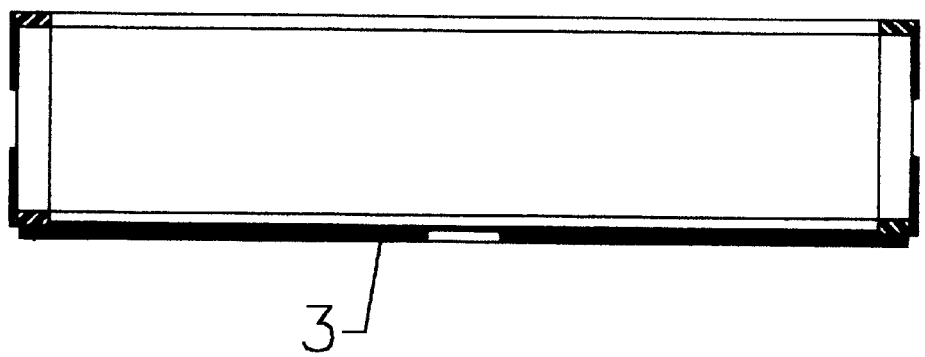
FIG. 2 is an end elevational view of the apparatus of FIG. 1.

Referring to the drawings FIG. 1, shows the drum assembly 1 which is created by assembling the pocket modules 2 and the shaft flange assembly 4 used for rotating the pocket assemblies. The drum flange 3 is shown in side view in FIG. 2 and provides an attachment point for the shaft flange assembly 4. The modules 2, which are self contained, are attached end-to-end using the concentricity stabilizer 14 of FIGS. 3 & 7, to form the outer surface of the drum 1. The drum, thus constructed, is self supporting and ready for connection to the drum flange 3 and shaft assembly 4. This is a very unique and novel construction of which is not anticipated nor described in the prior art.

Figure 3:
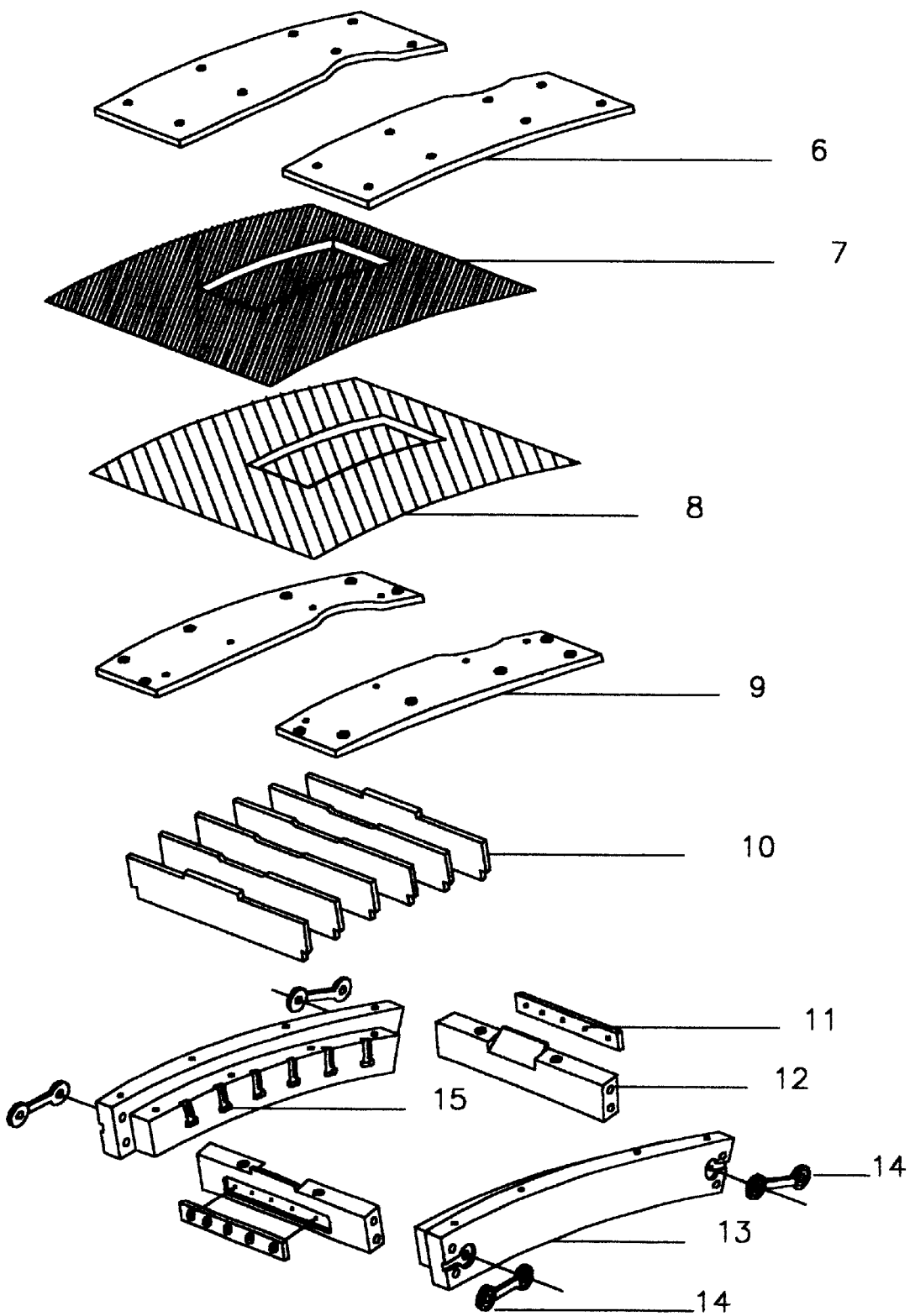
FIG. 3 shows the assembly of the components that comprise the modular pad forming assembly including the screen securing device.
Figure 3:
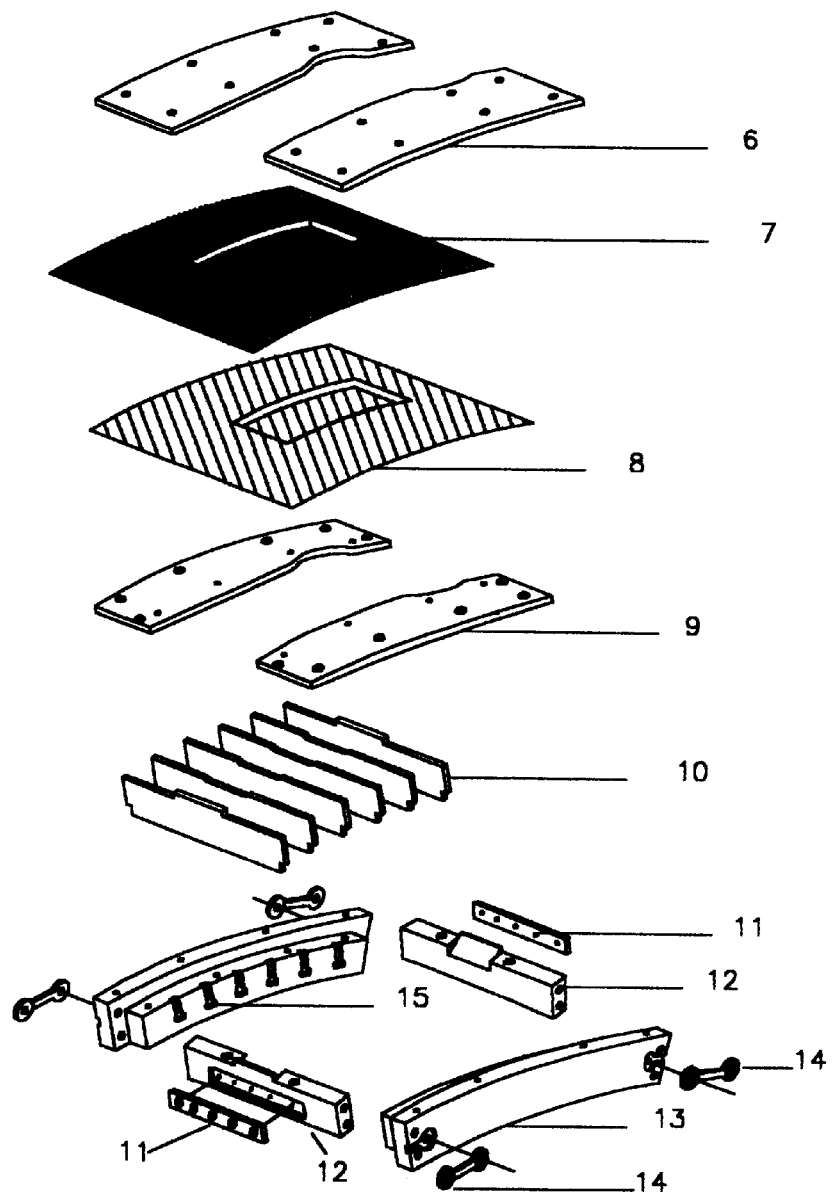
Figure 3:
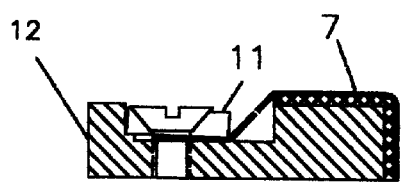

FIG. 3, an exploded view of the pocket modules, shows the assembly and alignment of the components which comprise the basic pad forming module. The pad forming module shown in FIG. 3 is constructed from two end rails 12 and two side rails 13 which form the basic structure of the module and to which the remaining module components are attached. The cross directional airflow control louvers 10 are inserted in radial slots 15 formed in the inner surface of the side rails 13. The sub-plates 9 are attached to the end and side rails on their outer perimeters. The forming screen or foraminous layer 7 and the foraminous support layer 8 are held to the end rails by the tilt-lock screen straps 11. The top plates 6 are attached to the end rail 12 and side rail 13 assembly by screws or other replaceable fastener means which also pass through the subplates 9 thus securing the forming screen or foraminous layer 7 and the foraminous support layer 8. The modules are then assembled end-to-end using the concentricity stabilizer 14. The novel concentricity stabilizer 14 acts as both a structural coupling and alignment device and a means for providing a concentric structure with in accepted industrial standards for roundness.

Figure 4:
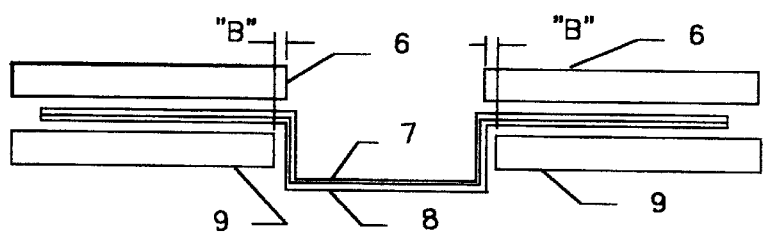
FIG. 4 shows the off-set created between the top plates and sub-plates.

The inner circumferential edge of the sub-plates 9 are off-set from the inner circumferential edge of the top plates by a specific distance which is related to the thickness of the pad to be formed. This off-set B shown in FIG. 4 provides sufficient clearance for air flow along the sides of the pad and eliminates local turbulence. Reference to FIG. 4 shows the off-set relationship of the top plates to the sub-plates and screens and the specific plate off-set B. Experimentation has proved that the offset distance should not be greater than 10 millimeters.

Figure 5:
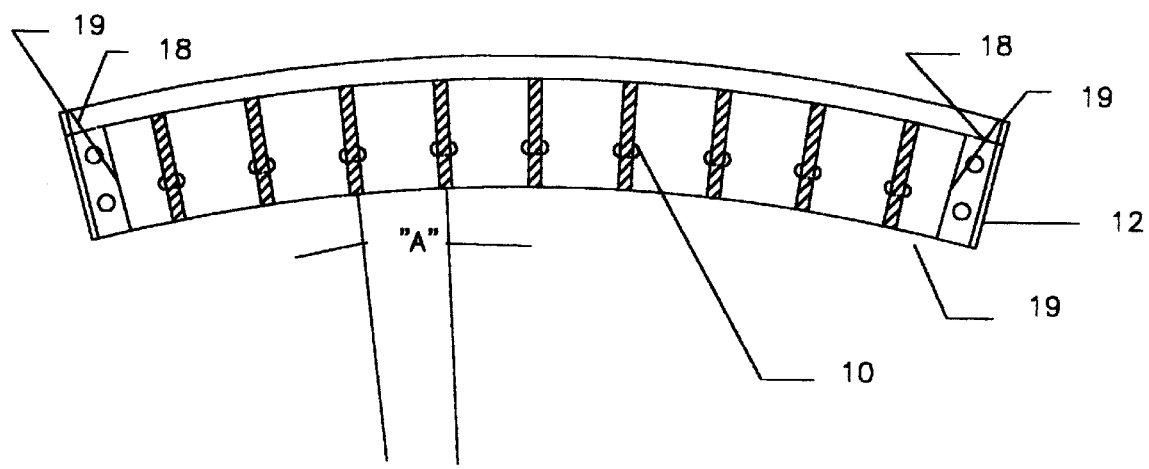
FIG. 5 shows the spacing of the cross directional guide airflow control louvers in accordance with the invention.

The cross directional radial airflow control louvers 10 which are provided at a specified angular relationship as shown in FIG. 5. The spacing relationship A is expressed as a function of the inner diameter of the drum as measured at the outside end of the airflow control louver. The spacing distance A is measured in inches and must meet the relationship of equation 1 which is spacing distance $A=\pi d/120 \pm \pi d/360$ where d equals the drum inner diameter. As an example, a standard 46 inch inner diameter drum would have an optimum angle of three degrees plus or minus one degree between any two airflow control louvers or a spacing distance of 1.2 inches plus or minus 0.4 inches as measured at the inner drum diameter. It has been determined through experimentation that there is a lower limit in that the spacing distance must not be less than 0.5 inches for best results and to prevent choking the air flow.

Figure 6:
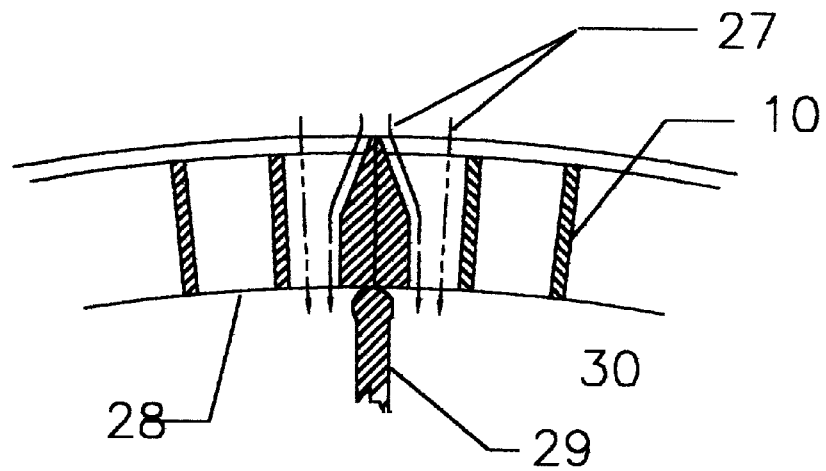
FIG. 6 shows the ends of the pockets and the joint created to smooth air flow during transition across the low pressure boundary.

Referring to FIG. 6, in operational practice, the inner wall 41 of the drum 1 of FIG. 1 is sealingly related to the low pressure system or plenum 30 by a seal wiper 29 such that the low pressure draws fiberized pulp or fiber into the pocket. Only one such seal connection is shown in the FIG. 6 but in practice, and as is well known to those versed in the art, as many as four or more low pressure sources may be provided. The air flow contours 27 indicate the air flow path. It was also discovered, during testing, that tapering that portion of the end plates that project into the airflow further reduced eddies and turbulence at the ends of the pad forming pockets. This additional invention for gas flow regulating was found to work best when the inner cross-directional radial edge of each end-rail, which describes the ends of the pad forming pocket, is tapered such that the angle of the taper 18, as shown in FIG. 5 is at least 15 degrees but no greater than 45 degrees as measured from the radial edge of the end plate 12 and wherein the land 19 formed at the outer radial edge is at least 0.060 inches in circumferential width.

Figure 7:
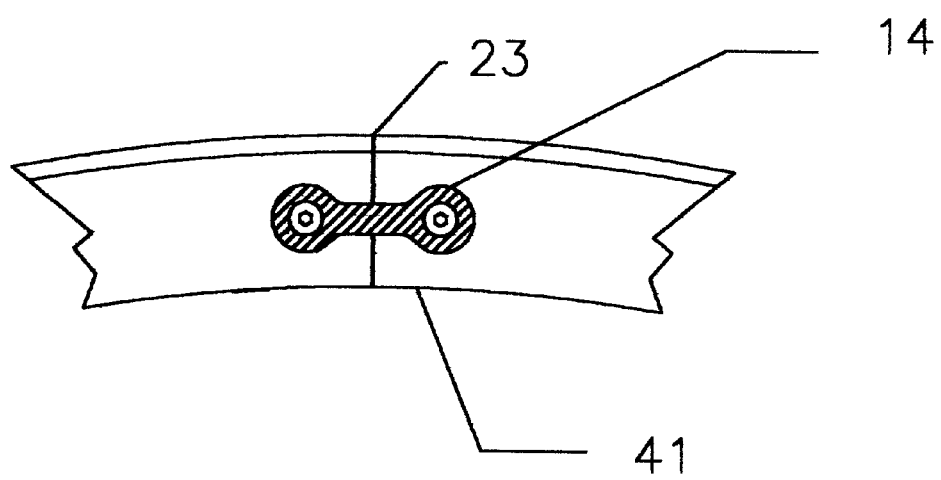
FIG. 7 is a plan view of the concentricity stabilizer.

FIG. 7 shows the concentricity stabilizer 14 as installed between two consecutive modules and which creates the joint 23. The use of the concentricity stabilizer permits the creation of the outer drum without the use of side plates, circular rings or other extraneous mechanical supports. Flanges 3 such as shown in FIG. 1 are added to adapt the modular drum former to whatever drum former system that may be required by the competitive design.

Figure 8:
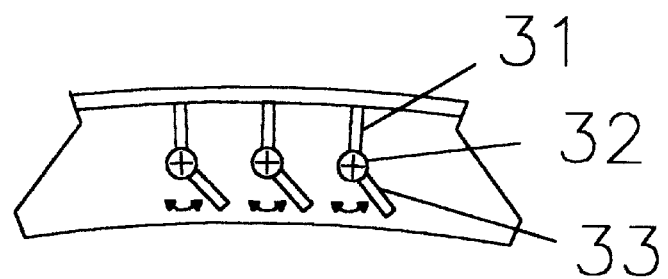
FIG. 8 shows a side view of the adjustable airflow control louver.
Figure 9:
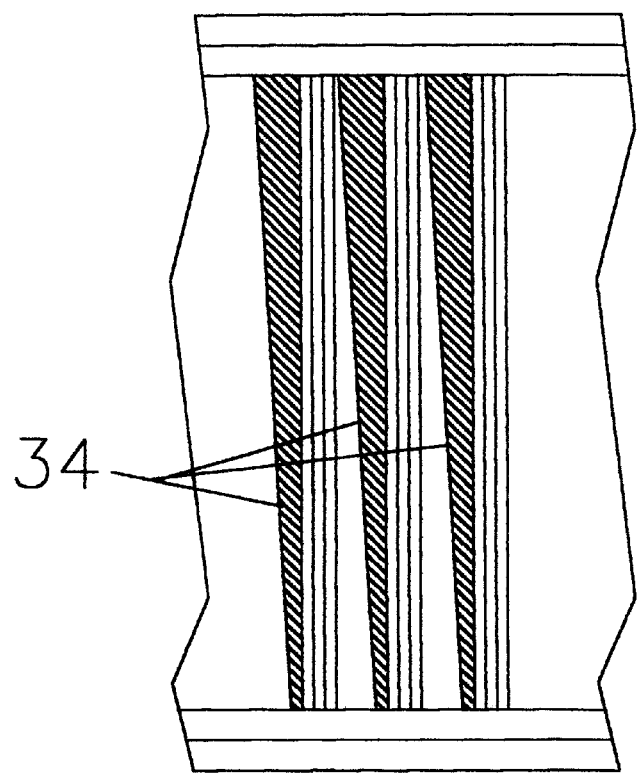
FIG. 9 shows a plan view of the adjustable airflow control louver having a linearly reduced profile.

Referring to FIG. 8, a modified adjustable airflow control louver 31 is shown where the lower end of the airflow control louver or the adjustable louver 33 is hinged and rotatable around the hinge point 32. In practice this system permits precise control of air flow at any point across the length of the pad former module. This is especially important where in the case of pad former conversions where there is a variation of pressure and consequently air flow across the width of the pad on the low pressure side of the drum FIG. 9 shows how the use of a special profile 34 of the adjustable louver 33 can create a change in air flow from one side of the pad former to the other thus adjusting for poor low pressure distribution in the equipment in which the modular drum former is installed. The adjustable louver can be made in a number of profile sections depending on the particular requirement.

Figure 10:
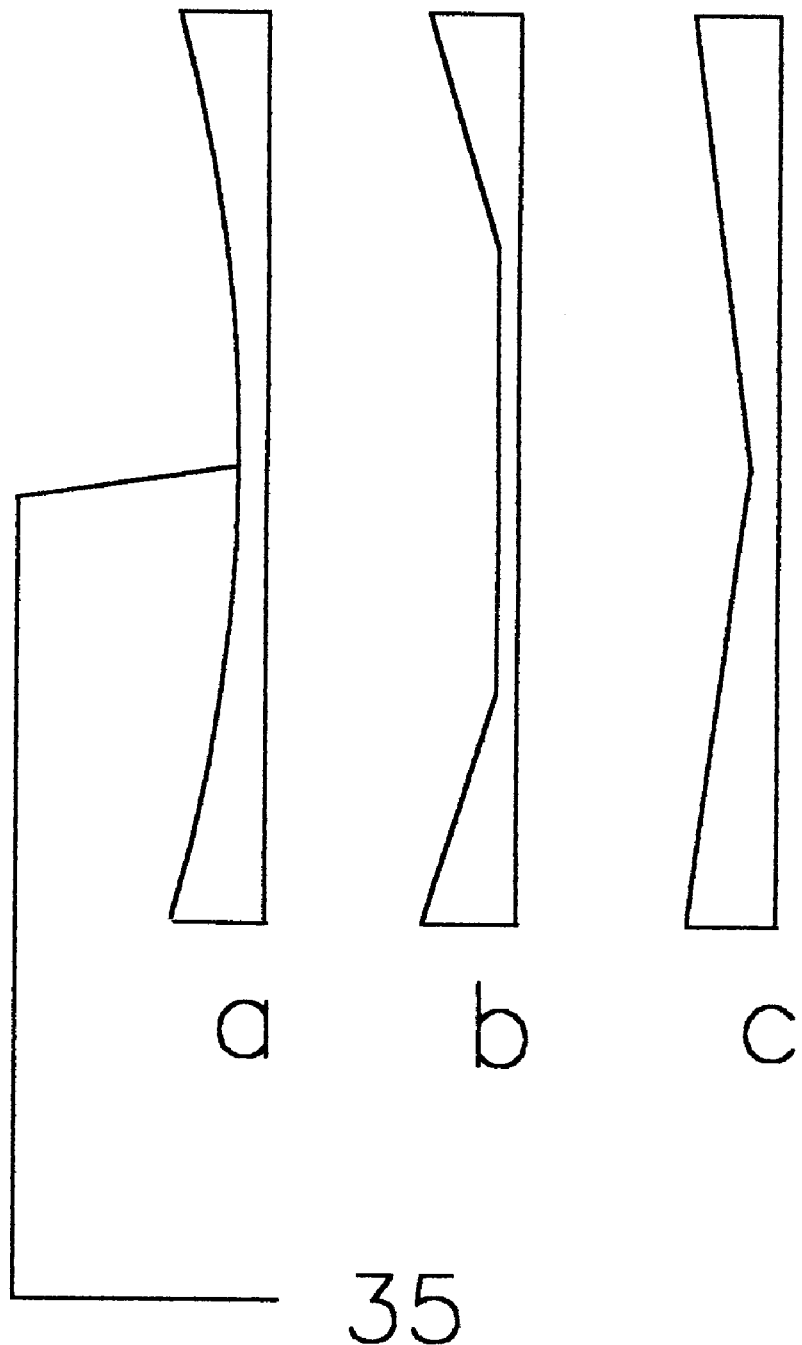
FIG. 10 shows some of the cross directional profiles that may be incorporated in the adjustable airflow control louver.

FIG. 10 shows several profiles. In FIG. 10a the profile 35 of the adjustable louver is parabolic and can be used to create a heavier pad center or to concentrate superabsorbent fiber or granules in the center section. FIGS. 10b and 10c show alternative profiles that can be used to tailor the air flow at specific points on the pad thus changing the density and weight per square inch across the width of the pad as required. Adjustable louvers can be used with standard fixed louvers as required to change density and weight per square inch in the axial and lateral directions of the pad. Louvers can be constructed from any suitable material.

Having described the invention in detail, it will be readily apparent that various changes and modifications can be made without departing from the essence of this invention. Any such changes and modifications are all contemplated as being within the scope of the present invention as defined by the following claims.

We claim:

1. An apparatus for forming discrete fibrous pads, said apparatus compromising:
   a. a drum constructed from a multiplicity of self contained pad formation pocket modules, said modules containing contiguous pad forming pockets, wherein said pockets have a three-dimensional configuration describing the pad to be formed therein, and being defined by a three-dimensional foraminous pad forming layer and which is supported by a lower foraminous support layer; and,
   b. a gas flow regulating system comprising a multiplicity of precisely positioned cross directional airflow control louvers which are fixed beneath the pad forming layer in a laterally radial position; and,
   c. a top plate and sub-plate assembly which defines the periphery of said pad forming pocket and which holds and contains within the top plate and sub-plate said three-dimensional foraminous pad forming layer and said lower foraminous support layer, said plate assembly being fixed to said end rails and to said side rails on said rail's outer edges by an attachment means, wherein said plates, which extend the full length of said side rail, thereby secure said airflow control louvers in place in said radial slots located in said side rail's inner surfaces; and
   d. a secondary gas regulating system created by off-setting the inner circumferential edges of said sub-plates towards the outer circumferential edge of the frame rails by distance of up to 10 millimeters; and,
   e. a gas flow regulating device wherein the inner cross-directional radial edge of each of said end-rails, which describes the ends of the pad forming pockets, are tapered such that the angle of the taper is at least 15 degrees but no greater than 45 degrees as measured from the lateral radial surface of said end rail and wherein the land formed at the other outermost radial edge is at least 0.060 inches in width.

2. A securing apparatus for said three-dimensional foraminous pad forming layer and said lower foraminous support layer of claim 1 incorporated in the end rails of claim 1 wherein said apparatus comprises:
   a. a relieved section located in the outside surface, parallel to the cross direction of the drum, of each end rail wherein said relieved section has two depths wherein said first depth, which is located at the lower radial point of said end rail, is less deep than the second depth which is located at the upper radial point of said end rail; and
   b. a clamp strap which fits within said relieved section and is provided with one or more openings in its lateral surface to accept fastening means fitted into threaded holes in the deeper section wherein the lateral edge of said clamp strap is pivoted off the shallower relieved section.

3. The airflow control louvers of claim 1 wherein the peripheral spacing distance, as measured from the cross directional center lines of any two adjacent airflow control louvers, is equal to the inside diameter of the drum times the circumference of said drum divided by 120 plus or minus one-third of said peripheral spacing distance except that the minimum distance shall not be less than 0.5 inches.

4. The airflow control louvers of claim 1 wherein the thickness of said airflow control louvers is at least 0.1 inches.

5. The airflow control louvers of claim 1 wherein the horizontal cross-section of said airflow control louvers is uniform.

6. The airflow control louvers of claim 1 wherein the horizontal cross section of said airflow control louvers is non uniform.

7. The airflow control louvers of claim 1 wherein the vertical cross-section of said airflow control louvers is uniform.

8. The airflow control louvers of claim 1 wherein the vertical cross section of said airflow control louvers is non uniform.

9. The airflow control louver of claim 1 wherein said airflow control louver contains a secondary airflow control louver affixed to the lower lateral edge of said airflow control louver by a pivotal hinge means and which is rotatable around an axis parallel to the lower lateral edge of said airflow control louver.

10. The secondary airflow control louver of claim 9 wherein said secondary airflow control louver's radial height may vary across the width of the airflow control louver.

11. The secondary airflow control louver of claim 9 wherein a locking means is provided to fix the rotary position of said secondary airflow control louver.

12. The apparatus of claim 1 wherein the louvers for each modulus comprise a combination of fixed and adjustable louvers.

* * * * *